United States Patent
Gerlitz

(10) Patent No.: US 8,401,604 B2
(45) Date of Patent: Mar. 19, 2013

(54) APPARATUS AND METHODS FOR NON-INVASIVE MEASUREMENT OF A SUBSTANCE WITHIN A BODY

(75) Inventor: Jonathan Gerlitz, Herzliya (IL)

(73) Assignee: Glucovista, LLC, Fairfield, NJ (US)

( * ) Notice: Subject to any disclaimer, the term of this patent is extended or adjusted under 35 U.S.C. 154(b) by 1287 days.

(21) Appl. No.: 12/101,859

(22) Filed: Apr. 11, 2008

(65) Prior Publication Data
US 2009/0259407 A1    Oct. 15, 2009

(51) Int. Cl.
*A61B 5/1455* (2006.01)
*A61B 6/00* (2006.01)

(52) U.S. Cl. ........ 600/316; 600/310; 600/322; 600/326; 600/473

(58) Field of Classification Search .................. 600/310, 600/316, 322, 326, 331, 340, 473
See application file for complete search history.

(56) References Cited

U.S. PATENT DOCUMENTS

| | | | |
|---|---|---|---|
| 4,041,932 A * | 8/1977 | Fostick | 600/326 |
| 5,313,941 A | 5/1994 | Braig et al. | |
| 5,370,114 A | 12/1994 | Wong et al. | |
| 5,515,847 A | 5/1996 | Braig et al. | |
| 5,553,613 A * | 9/1996 | Parker | 600/316 |
| 5,601,079 A | 2/1997 | Wong et al. | |
| 5,615,672 A | 4/1997 | Braig et al. | |
| 5,666,956 A | 9/1997 | Buchert | |
| 6,002,953 A * | 12/1999 | Block | 600/316 |
| 6,067,463 A * | 5/2000 | Jeng et al. | 600/310 |
| 6,949,070 B2 | 9/2005 | Ishler | |
| 6,998,247 B2 | 2/2006 | Monfre et al. | |
| 7,183,102 B2 | 2/2007 | Monfre et al. | |
| 2005/0038344 A1 * | 2/2005 | Chance | 600/322 |
| 2005/0043630 A1 | 2/2005 | Buchert | |
| 2006/0263916 A1 * | 11/2006 | Arno | 438/14 |
| 2007/0106139 A1 | 5/2007 | Nagata et al. | |
| 2007/0197885 A1 | 8/2007 | Mah et al. | |

OTHER PUBLICATIONS

International Search Report from Korean Intellectual Property Office dated Nov. 2, 2009 for International Application No. PCT/US2009/037829.
Written Opinion from Korean Intellectual Property Office dated Nov. 2, 2009 for International Application No. PCT/US2009/037829.
English translation of Office Action dated Aug. 3, 2012 from State Intellectual Property Office of P.R.C. for Chinese Application No. 200980112612.7.

* cited by examiner

*Primary Examiner* — Eric Winakur
*Assistant Examiner* — Chu Chuan (J J) Liu
(74) *Attorney, Agent, or Firm* — Klein, O'Neill & Singh, LLP

(57) ABSTRACT

Embodiments of the present system and methods measure a concentration of a substance, such as glucose, in a body. The present embodiments measure a first amount of infrared (IR) radiation absorbed or emitted from the body in a first wavelength band, and a second amount of IR radiation absorbed or emitted from the body in a second wavelength band. The present embodiments also measure a temperature at a surface of the body and an ambient temperature. A normalized ratio parameter is calculated from the four measurements, and the concentration of the substance in the body is calculated by correlating the normalized ratio parameter with the body surface temperature and the ambient temperature using an empirically derived lookup table. Also disclosed are methods for creating the empirically derived lookup table.

17 Claims, 7 Drawing Sheets

APPARATUS AND METHODS FOR NON-INVASIVE MEASUREMENT OF A SUBSTANCE WITHIN A BODY

BACKGROUND OF THE INVENTION

1. Field of the Invention

The present invention relates to measurement of a substance, such as glucose, within a body, such as the human body.

2. Description of Related Art

Several patents suggest methods to non-invasively measure the concentration of a substance, such as glucose, in the bloodstream. Examples include U.S. Pat. Nos. 5,313,941; 5,370,114; 5,515,847; 5,601,079; 5,615,672; 5,666,956; 6,949,070; 6,998,247; and 7,183,102. However, the methods disclosed in these patents do not adequately consider the body surface temperature at the point of measurement and the ambient temperature. Both of these parameters affect the accuracy of the substance concentration measurement in the mid to far infrared spectrum.

SUMMARY OF THE INVENTION

The preferred embodiments disclosed herein have several features, no single one of which is solely responsible for their desirable attributes. Without limiting the scope of the present embodiments as expressed by the claims that follow, their more prominent features now will be discussed briefly.

One embodiment of the present disclosure is a method for measuring a concentration of a substance in a body. The method comprises the steps of measuring a first amount of infrared (IR) radiation absorbed or emitted from the body in a first wavelength band, and measuring a second amount of IR radiation absorbed or emitted from the body in a second wavelength band. The method further comprises the steps of measuring a temperature at a surface of the body, and measuring an ambient temperature. The method further comprises the steps of calculating a normalized ratio parameter based on the first amount, the second amount, the body surface temperature and the ambient temperature, and calculating the concentration of the substance in the body by correlating the normalized ratio parameter with the body surface temperature and the ambient temperature using an empirically derived lookup table.

Another embodiment of the present disclosure is a system for measuring a concentration of a substance in a body. The system comprises an infrared (IR) detector, and a filter assembly including at least a first filter and a second filter configured to filter IR radiation transmitted to the detector. The first filter is configured to transmit only a first amount of IR radiation absorbed or emitted from the body in a first wavelength band. The second filter is configured to transmit only a second amount of IR radiation absorbed or emitted from the body in a second wavelength band.

Another embodiment of the present disclosure is a method for creating an empirically derived lookup table by taking a series of measurements across a population. The method comprises the steps of a) directly measuring a concentration of a substance in the body for each member of the population, b) measuring a first amount of infrared (IR) radiation absorbed or emitted from the body in a first wavelength band for each member of the population, and c) measuring a second amount of IR radiation absorbed or emitted from the body in a second wavelength band for each member of the population. In steps d) and e), respectively, simultaneously with steps b) and c) a temperature at a surface of the body is measured and an ambient temperature is measured. The method further comprises the step of t) calculating a normalized ratio parameter based on the first amount, the second amount, the body surface temperature and the ambient temperature. In step g), steps a) through f) are repeated at a plurality of ambient temperatures and for a plurality of substance concentrations. In step h), the empirically derived lookup table is created by plotting the body surface temperature, the ambient temperature and the normalized ratio parameter for each member of the population at each ambient temperature and for each substance concentration.

BRIEF DESCRIPTION OF THE DRAWINGS

The preferred embodiments of the present disclosure now will be discussed in detail with an emphasis on highlighting the advantageous features. These embodiments depict the novel and non-obvious aspects of the disclosure shown in the accompanying drawings, which are for illustrative purposes only. These drawings include the following figures, in which like numerals indicate like parts.

DETAILED DESCRIPTION OF THE PREFERRED EMBODIMENTS

Embodiments of the present system and methods are configured to determine a concentration of a substance in a body. In certain embodiments, the measured substance may be glucose in the bloodstream. However, those of ordinary skill in the art will appreciate that the present system and methods may be used to measure concentrations of other substances, such as cholesterol for example. The present system and methods are advantageously non-invasive, and therefore avoid the discomfort of skin punctures.

To determine the substance concentration, the present embodiments measure infrared (IR) radiation emitted and/or absorbed from the body in different wavelengths and normalize these measurements against IR radiation emitted and/or absorbed from a blackbody. The present embodiments also measure the ambient temperature and the body surface temperature simultaneously with the IR radiation measurements. Ambient temperature and body surface temperature affect the accuracy of the IR radiation measurements, because they affect the equilibrium of heat transfer between the surrounding environment and the measured surface, and they also affect the probability of absorption or emission by the surface.

In certain embodiments the internal body temperature may be measured instead of, or in addition to, the body surface temperature. In the present disclosure and claims the term body surface temperature is used broadly to include either or both of the temperature at the body surface and the internal body temperature.

In the present embodiments, a ratio of the normalized IR radiation measurements results in a normalized ratio parameter. Using the normalized ratio parameter and measurements of the body surface temperature and the ambient temperature the present system and methods return the substance concentration in the body by referencing an empirically derived lookup table. The empirically derived lookup table, and example methods for creating such a table, are discussed in further detail below.

Figure 1:
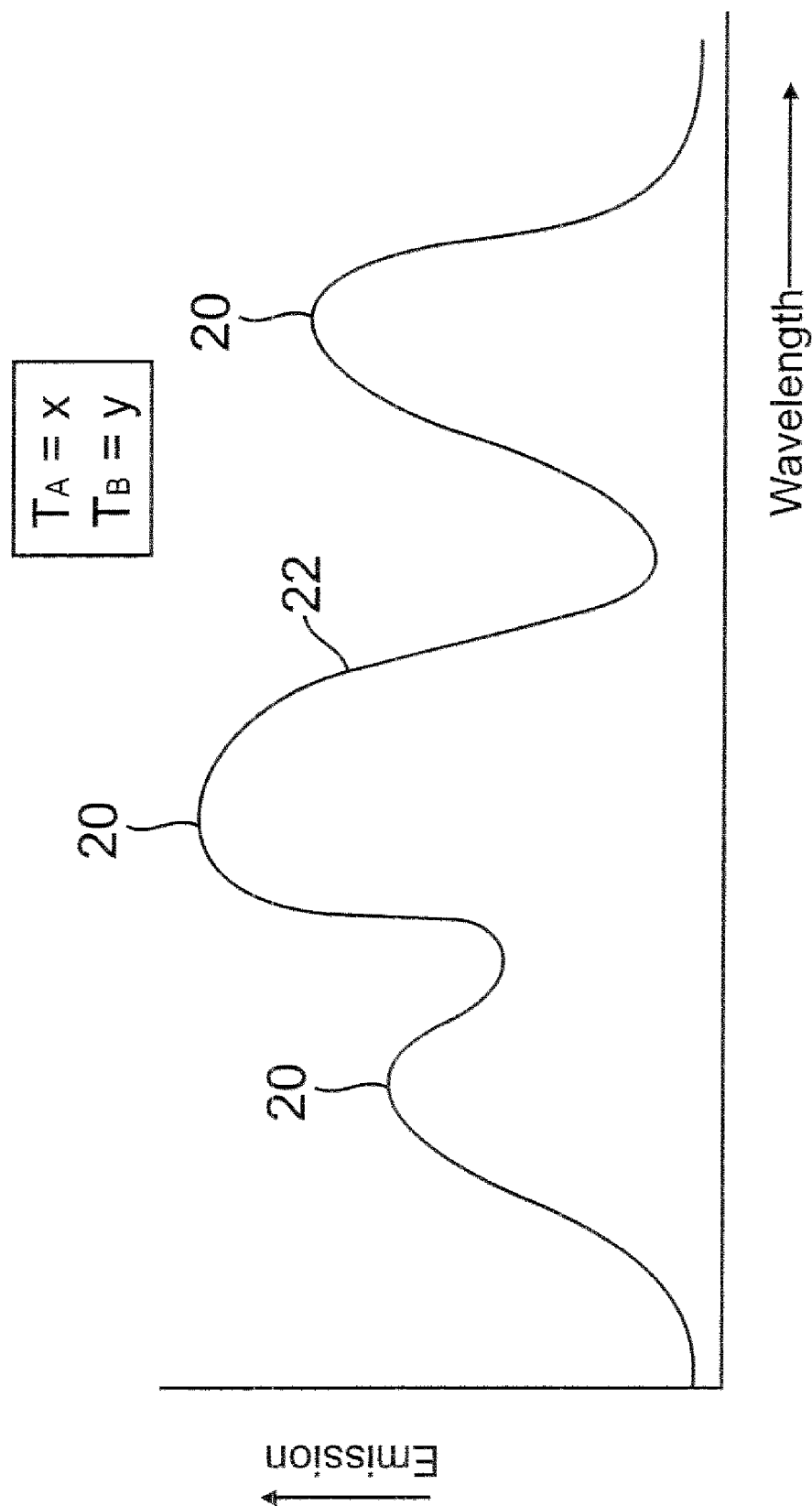
FIG. 1 is a plot of infrared (IR) radiation emitted from and absorbed by a hypothetical body across a given spectrum.

All bodies and all substances absorb and emit IR radiation. The magnitude of IR radiation absorbed and emitted at a given wavelength varies according to the body's temperature and the ambient temperature. FIG. 1 illustrates a sample plot of the IR emission spectrum for a hypothetical body, where the ambient temperature $T_A$ is equal to x and the body temperature $T_B$ is equal to y. As shown, the body more readily absorbs and emits IR radiation at certain wavelengths, represented by the peaks 20 in the curve 22.

In certain substances, IR absorption/emission is particularly distinctive in the far infrared (FIR). Glucose is one example. Thus, to measure the concentration of substances such as glucose in a body it is advantageous to measure the FIR radiation emitted by the body. As used herein, the term far infrared and the abbreviation FIR denote IR radiation at wavelengths greater than or equal to approximately 7 microns.

Embodiments of the present system and methods measure the FIR radiation absorbed or emitted by a body at different wavelength ban ds. The first wavelength band (or bands) is selected to be in a band (or bands) where the substance is known to have significant FIR absorption/emission. The second wavelength band is selected to be the entire FIR absorption/emission spectrum of the body. In an alternative embodiment, the second wavelength band (or bands) is selected to be in a band (or bands) where the substance is known to have no or negligible FIR absorption emission. After normalizing each measurement, their ratio can be used to determine the concentration of the substance in the body, as discussed in detail below.

Figure 2:
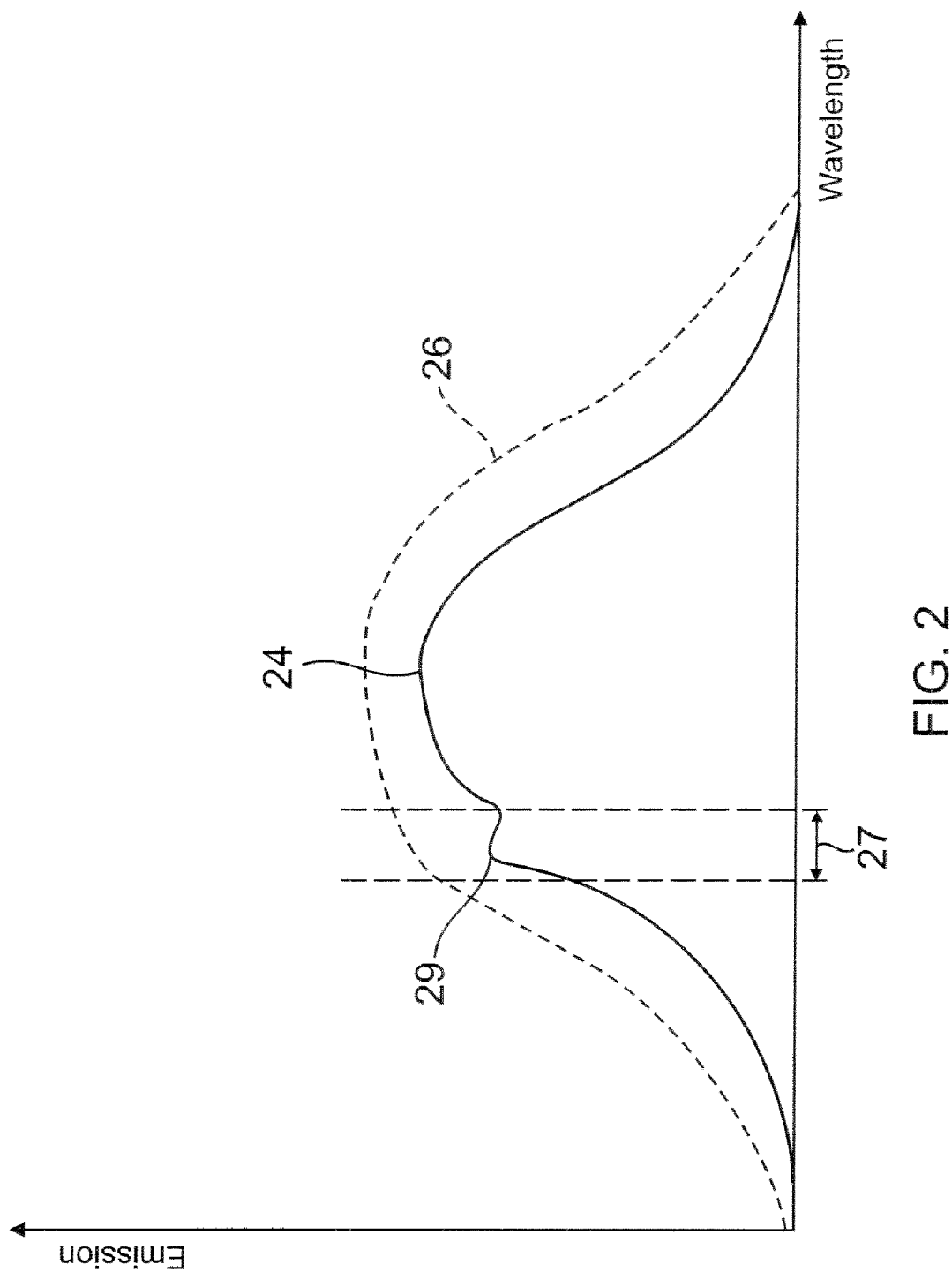
FIG. 2 is a plot of far infrared (FIR) radiation emitted from and absorbed by a hypothetical body and a blackbody across a given spectrum.

In the present embodiments, the FIR measurements are normalized against a blackbody. A blackbody, as those of ordinary skill in the art will appreciate, is one that absorbs and emits radiation with theoretical emissivity of one. FIG. 2 illustrates a sample plot of the FIR absorption/emission spectrum for a hypothetical body (solid curve 24) and for a blackbody (dashed curve 26). For both the body and the blackbody the ambient temperature $T_A$ is the same. Similarly, for both the body and the blackbody the body/blackbody temperature $T_B$ is the same. The dashed vertical lines represent a first wavelength band 27 in which the substance whose concentration is to be measured is known to have an FIR absorption/emission peak 29. For example, for glucose the selected band 27 may be between 9.3 microns and 9.9 microns.

In one embodiment of the present methods the FIR radiation absorbed/emitted by the body in the first wavelength band is measured and then normalized against the blackbody FIR radiation in the first wavelength band. The FIR radiation absorbed/emitted by the body over the entire FIR spectrum is then measured and normalized against the blackbody FIR radiation over the entire FIR spectrum. Measurements of the body surface temperature and the ambient temperature are taken simultaneously with the first and second FIR measurements. The ratio of the first and second normalized measurements yields a normalized ratio parameter. The concentration of the substance in the body is correlated with the normalized ratio parameter, the body surface temperature and the ambient temperature. In certain embodiments a logarithm, such as a natural logarithm (ln), of the normalized ratio parameter may be used in the correlation step. In the present embodiments, the correlation step includes referencing an empirically derived lookup table.

According to embodiments of the present system and methods, an empirically derived lookup table may be constructed by taking a series of measurements across a statistically representative population (hereinafter "the Group"). The measurements taken for each member of the Group include a concentration of the substance of interest (such as glucose) taken according to a conventional invasive method, a first amount of FIR radiation absorbed or emitted from the body in a first wavelength band, a second amount of FIR radiation absorbed or emitted from the body in a second wavelength band, a temperature at a surface of the body and an ambient temperature. The first wavelength band (which may comprise multiple bands) is selected to be in a band where the substance is known to have significant FIR absorption/emission. In one embodiment, the second wavelength band is selected to be the entire FIR absorption/emission spectrum of the body. In an alternative embodiment, the second wavelength band (or bands) is selected to be in a band (or bands) where the substance is known to have no or negligible FIR absorption/emission. The above measurement process is repeated in various ambient temperatures and for various substance concentrations.

The first and second FIR radiation measurements are normalized against a blackbody at the same temperature. The lookup table is then created by plotting three of the measured parameters against one another for all members of the Group. The three parameters are the body surface temperature, the ambient temperature and the ratio of the first normalized FIR measurement to the second normalized FIR measurement, referred to herein as a normalized ratio parameter. In certain embodiments a logarithm, such as a natural logarithm (ln), of the normalized ratio parameter may be plotted against the body surface temperature and the ambient temperature. If the population size is large enough an accurate reference table can be created that enables easy determination of the substance concentration in the body using only non-invasive measurements of FIR absorption/emission, ambient temperature and body surface temperature.

Figure 3:
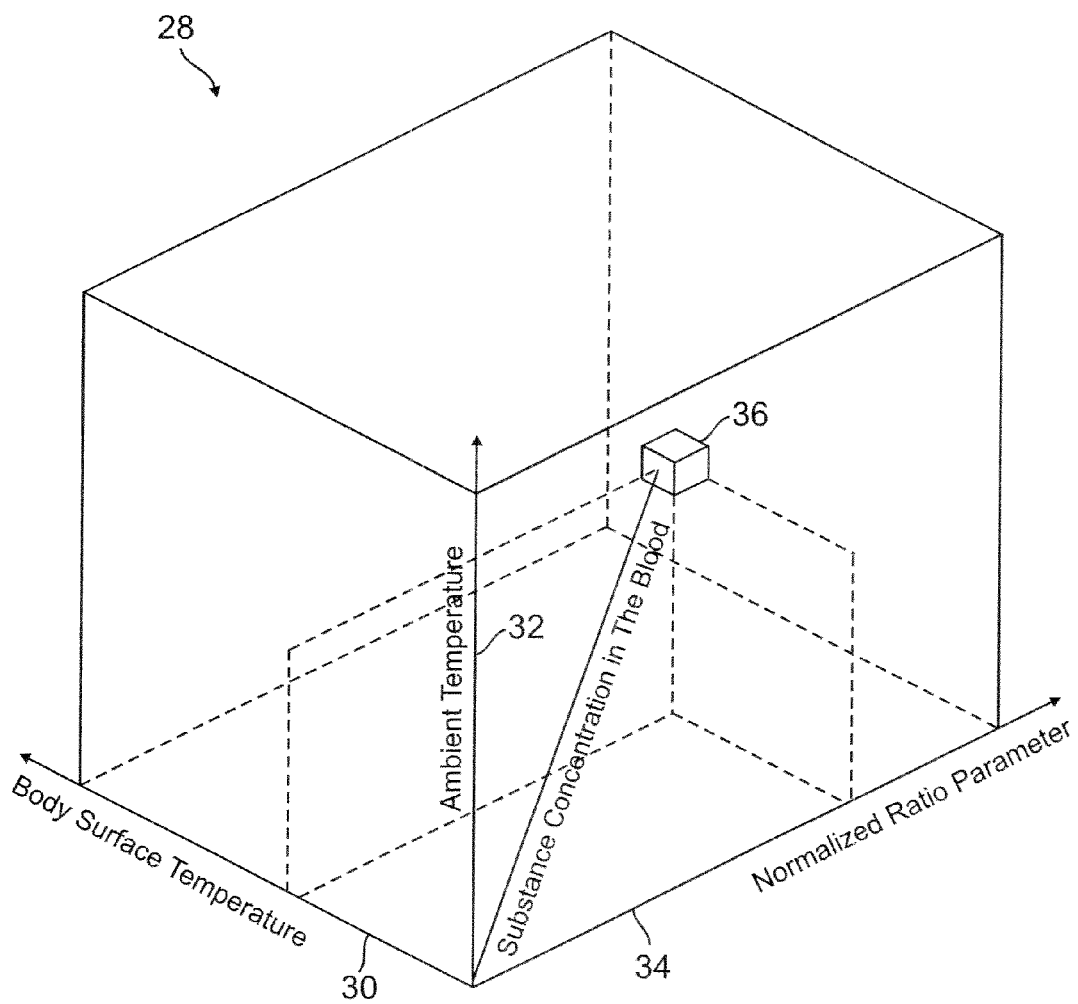
FIG. 3 is a conceptual perspective view of an empirically derived lookup table according to the present embodiments the table having as axes a body surface temperature, an ambient temperature and a normalized ratio parameter.

FIG. 3 illustrates a conceptual embodiment of the present empirically derived lookup table 28. In the illustrated embodiment, the table 28 comprises three axes: the body surface temperature 30, the ambient temperature 32 and the normalized ratio parameter 34. To determine the concentration of a given substance within the body, three measurements, corresponding to the three axes, are taken from a body. The intersection 36 of the three measurements in the table 28 yields the substance concentration as shown in FIG. 3.

In alternative embodiments, the lookup table may comprise a database containing a plurality of data points. The illustrated Cartesian plot of FIG. 3 is intended to help the reader visualize the relationships between the three parameters of the body surface temperature 30, the ambient temperature 32 and the normalized ratio parameter 34. However, those of ordinary skill in the art will appreciate that not all of the present embodiments need include a lookup table that is plotted in three-dimensional space.

The Applicant has not yet completed taking a series of measurements across a population in order to construct the empirically derived lookup table 28. These measurements are expected to yield a population distribution that will indicate to what extent FIR radiation readings will vary from one subject to the next under identical conditions (same substance concentration in bloodstream, same body surface temperature, same ambient temperature). If the results indicate that there is no or negligible variation, then embodiments of the present system 38 and methods can be used to determine the concentration of a substance in bloodstream without the need for any invasive measurements for each subject. However, if the results indicate that there is a substantial variation, then for each subject an initial measurement through conventional invasive methods may need to be taken in order to calibrate the system 38 and methods for that particular subject. Advantageously, however, only one or two invasive measurements are needed for the calibration.

Figure 4:
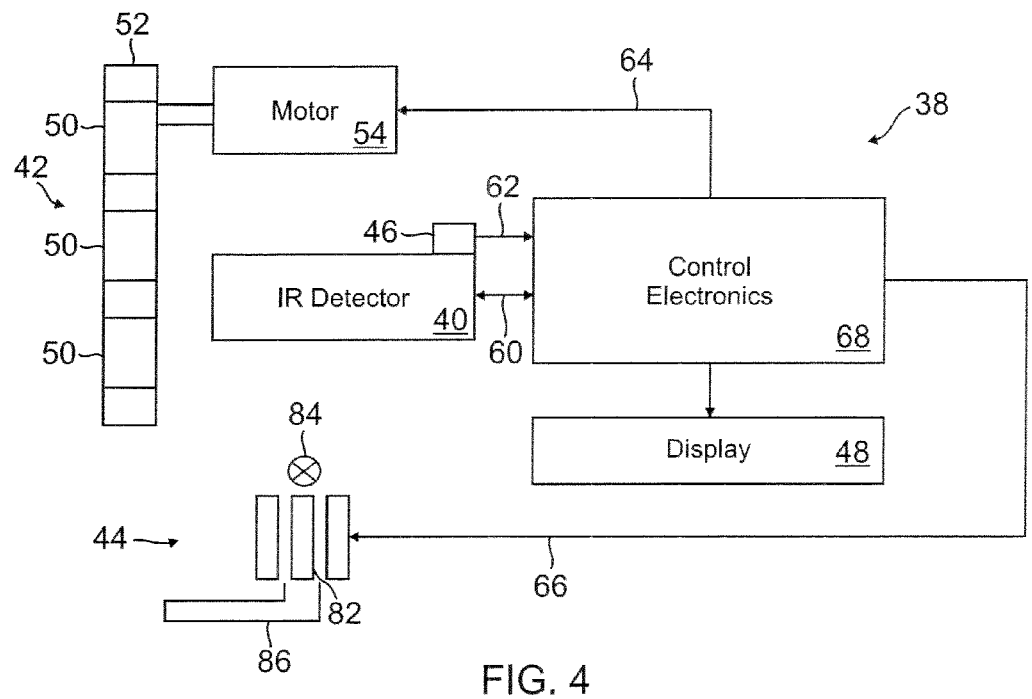
FIG. 4 is a schematic drawing of one embodiment of the present system for measuring a concentration of a substance in a body.

FIG. 4 illustrates, schematically, one embodiment of the present system 38 for measuring a concentration of a substance in a body. Broadly, the illustrated embodiment of the present system 38 comprises an IR radiation detector 40, an IR filter assembly 42 heating and/or cooling apparatus 44, and apparatus for measuring the ambient temperature 46. In the present embodiments the IR detector 40 measures the body surface temperature. However, those of ordinary skill in the art will appreciate that alternative apparatus for measuring the body surface temperature may be used.

In one embodiment the IR detector 40 is a thermopile with collimating optics. However, those of ordinary skill in the art will appreciate that the JR detector could comprise a different type of detector, such as a bolometer. The illustrated system 38 further comprises a display 48 for presenting information such as the substance concentration, the measured parameters and other information. In certain embodiments the display 48 may be a liquid crystal display (LCD).

With continued reference to FIG. 4, the IR filter assembly 42 is positioned in front of the detector 40. In the illustrated embodiment, the IR filter assembly 42 comprises three filters 50, although those of ordinary skill in the art will appreciate that the IR filter assembly 42 could include any number of filters. A first one of the filters 50 transmits only the spectral band in which the substance exhibits significant absorption/emission of IR radiation. A second one of the filters 50 transmits part of the spectral band in which the substance has no or negligible absorption/emission. A third one of the filters 50 transmits all of the IR radiation related to the body's temperature. The third filter 50 may transmit, for example, all of the IR radiation between approximately 7 microns and approximately 15 microns.

In the illustrated embodiment, the IR filter assembly 42 includes a filter wheel or drive 52 and a motor 54. In certain embodiments, the motor 54 may comprise a solenoid. The motor 54 or solenoid is configured to provide a motive force for changing a position of the filter assembly 42 with respect to the IR detector 40. Activation of the motor 54 or solenoid enables the filters 50 to be sequentially positioned in front of the detector 40 as each JR radiation measurement is taken.

Figure 5:
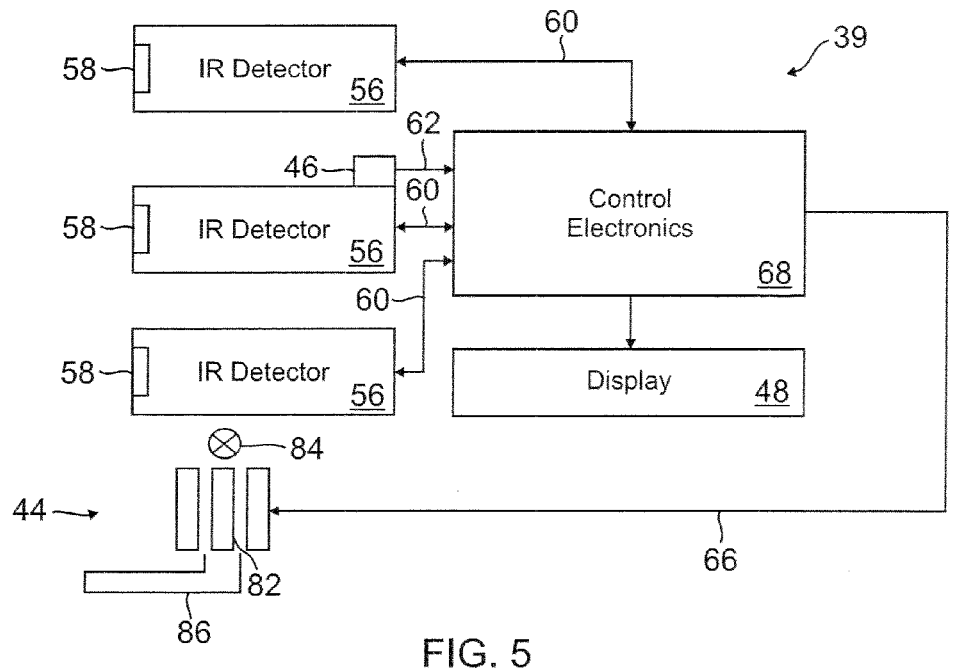
FIG. 5 is a schematic drawing of another embodiment of the present system for measuring a concentration of a substance in a body.

In an alternative embodiment of the present system 39 illustrated in FIG. 5, the motor 54 and the filter assembly 42 are replaced with a plurality of fixed position IR detectors 56. In the illustrated embodiment, three IR detectors 56 are shown. However, those of ordinary skill in the art will appreciate that any number of IR detectors may be provided. In the embodiment of FIG. 5, each IR detector 56 includes its own JR filter 58. The filters 58 may, for example, be substantially similar to the three filters 50 provided in the embodiment of FIG. 4 with respect to the wavelengths of JR radiation that they transmit. In the embodiment of FIG. 5, there are advantageously no moving parts in the detector/filter assembly, and all measurements may be made simultaneously.

With reference to FIGS. 4 and 5, the illustrated embodiments of the present system 38, 39 include apparatus for measuring ambient temperature 46. In certain embodiments the ambient temperature measuring apparatus 46 may be a thermistor, such as a negative temperature coefficient (NTC) thermistor. For simplicity, the ambient temperature measuring apparatus will be referred to herein as a thermistor. However, those of ordinary skill in the art will appreciate that the ambient temperature measuring apparatus 46 may be any apparatus that is suitable for measuring ambient temperature, such as a thermocouple. While in the illustrated embodiments the thermistor 46 is attached to the IR detector 40, 56, those of ordinary skill in the art will appreciate that it need not be. In certain embodiments the thermistor 46 measures the temperature of a housing (not shown) of the IR detector 40, 56, which normally is equal to ambient temperature.

Figure 6:
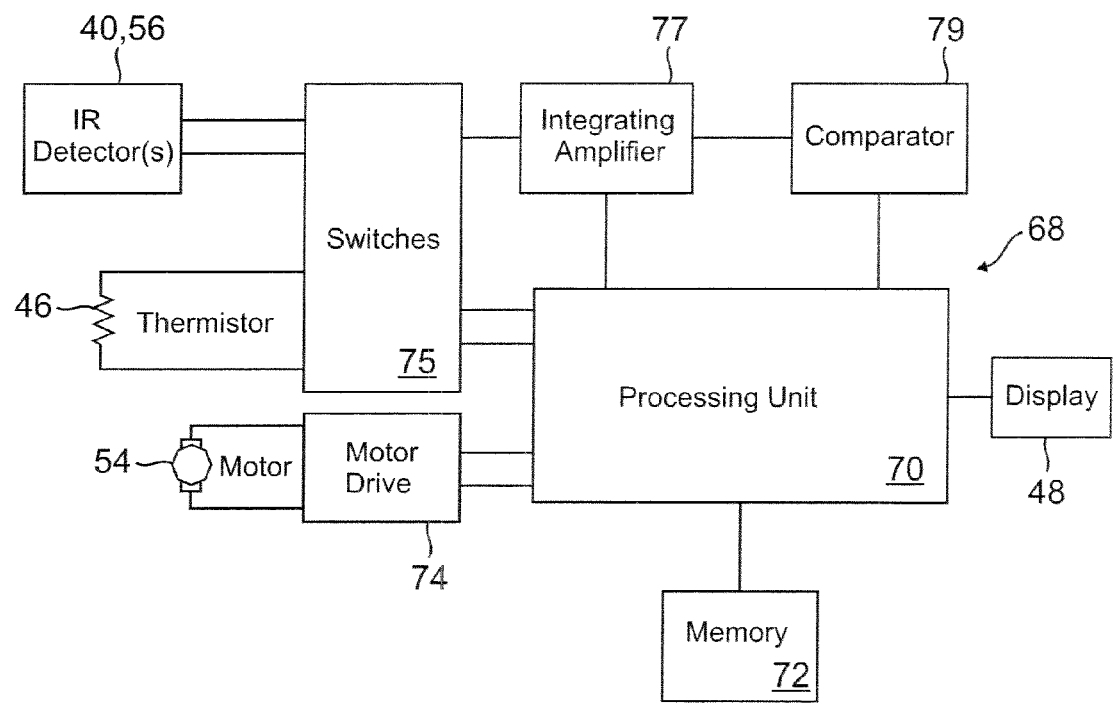
FIG. 6 is a schematic drawing of control electronics for the systems of FIGS. 4 and 5.

With continued reference to FIGS. 4 and 5, outputs 60, 62 of the IR detector(s) 40, 56 and the thermistor 46 and control inputs 64, 66 of the motor 54 and the heating/cooling apparatus 44 are connected to control electronics 68. FIG. 6 illustrates further details of the control electronics 68, which include a processing unit 70 and memory 72. The memory 72 may include the lookup table 28 and/or other look up tables for calculating results of the measurements taken by the present system 38, 39. The processing unit 70 may comprise a central processing unit (CPU) running software and/or firmware. Alternatively, the processing unit 70 may comprise one or more application-specific integrated circuits (ASICs). The processing unit 70 processes signals from the IR detector(s) 40, 56 and the thermistor 46. The processing unit 70 also drives the display 48 to show results that may include the substance concentration, the measurements taken by the JR detector(s) 40, 56 and/or the thermistor 46, and other information. In the embodiment of FIG. 6, the processing unit 70 also controls a motor drive 74, which in turn controls the motor 54 to change the position of the filter assembly 42 with respect to the IR detector 40.

With reference to FIG. 6, the illustrated control electronics 68 include one or more switches 75 for switching between measurement channels. For example, the switches 75 might change between a first channel that carries a signal from the IR detector 40, 56 and a second channel that carries a signal from the thermistor 46. The processing unit 70 controls the switches 75.

With continued reference to FIG. 6, the illustrated control electronics 68 further include an integrating amplifier 77. The integrating amplifier 77 amplifies a voltage generated by the IR detector 40, 56 to a measurable value. The voltage generated by the IR detector 40, 56 is proportional to the detected body radiation, and may be very small. The illustrated control electronics 68 further include a comparator 79. The comparator 79, together with the integrating amplifier 77 converts the voltage from the IR detector 40, 56 into a time interval that is inversely proportional to the input voltage and is measured by the processing unit 70.

With reference to FIGS. 4 and 5, in certain embodiments the heating/cooling apparatus 44 comprises a Peltier element 82 configured to provide a desired amount of heat or cold, a fan 84 to drive the heated or cooled air, and a funnel 86 to direct the heated or cooled air onto the body surface. Applying heat or cold to the skin surface stimulates the absorption or emission of IR radiation by the substance whose concentration is to be measured. In the case of glucose, for example, cooling the skin stimulates the absorption of IR radiation while heating the skin stimulates the emission of IR radiation. In another embodiment, a flow of ambient temperature air stimulates emission or absorption. In such an embodiment the heating/cooling apparatus 44 may be replaced with an airflow apparatus to drive the ambient air.

Figure 7:
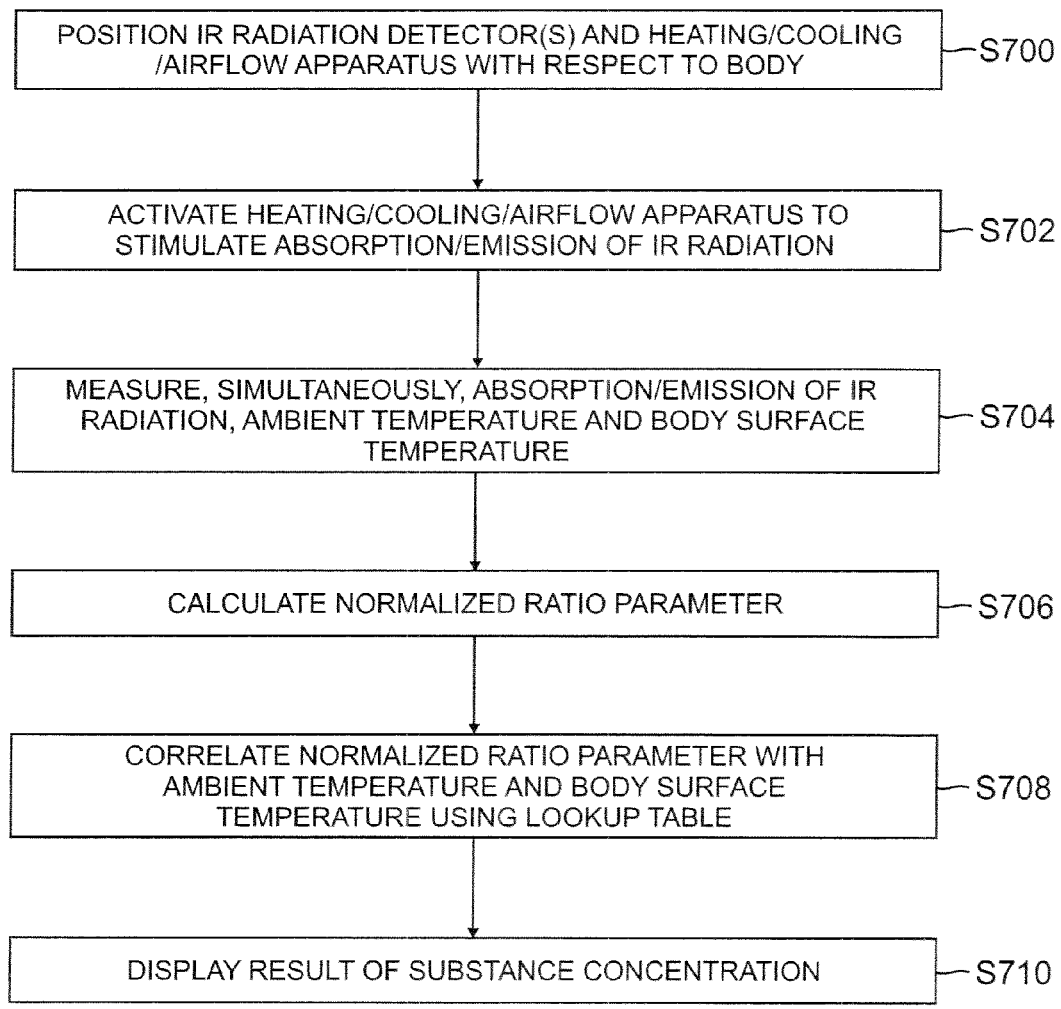
FIG. 7 is a process flow chart illustrating one embodiment of the present method for measuring a concentration of a substance in a body.

The process flowchart of FIG. 7 illustrates one embodiment of the present methods for measuring the concentration of a substance within a body. At step S700 the IR radiation detector(s) and the heating/cooling/airflow apparatus are positioned with respect to the body. At step S702 the heating/cooling/airflow apparatus is activated to stimulate absorption/emission of IR radiation by the substance. At step S704 the absorption/emission of IR radiation, ambient temperature and body surface temperature are measured simultaneously. Step S704 is repeated to obtain IR radiation measurements in first and second wavelength bands, as discussed above. At step S706 the normalized ratio parameter is calculated from the IR radiation measurements. At step S708 the normalized ratio parameter is correlated with the ambient temperature and the body surface temperature using the lookup table 28. And at step S710 the substance concentration is displayed.

With either embodiment of the system 38, 39 shown in FIGS. 4 and 5, an alternative method of measuring the absorption/emission of IR radiation, the ambient temperature and the body surface temperature is to scan the body surface while taking multiple measurements at various points on the body surface. Software, for example, may then be used to identify the most desirable result from the plurality of measurements. Parameters for selecting the most desirable result may be, for example, repeatability, maximum signal, etc.

Figure 8:
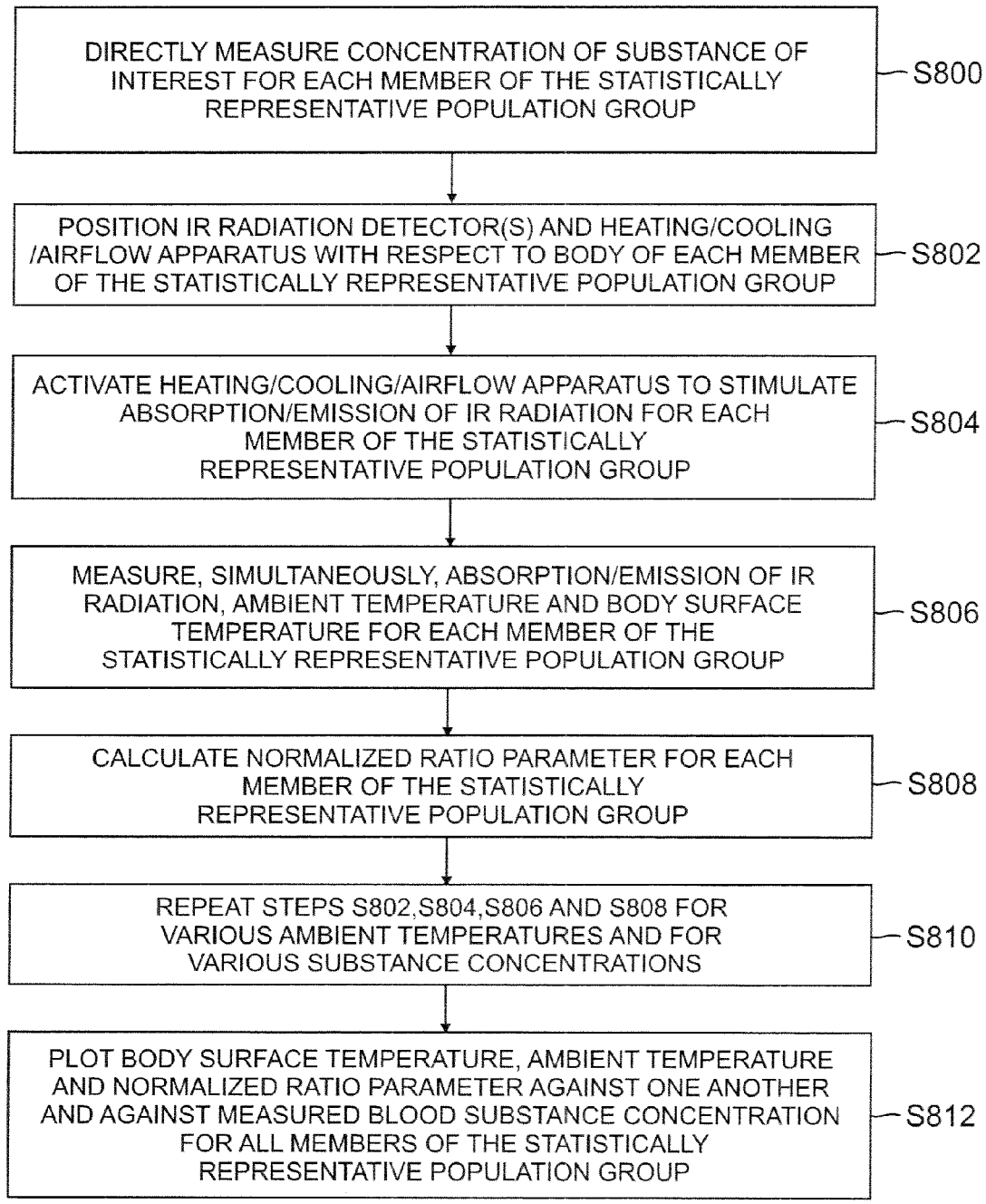
FIG. 8 is a process flow chart illustrating one embodiment of the present method for constructing an empirically derived lookup table.

The process flowchart of FIG. 8 illustrates one embodiment of the present methods for constructing an empirically derived lookup table 28. At step S800 a concentration of a substance of interest (such as glucose) is directly measured for each member of the Group. This step may, for example, involve drawing a sample of blood from each member and testing the blood according to any known method. At step S802 the IR radiation detector(s) and the heating/cooling/airflow apparatus are positioned with respect to the body of each member of the Group. At step S804 the heating/cooling/airflow apparatus is activated to stimulate absorption/emission of IR radiation by the substance for each member of the Group. At step S806 the absorption/emission of IR radiation, ambient temperature and body surface temperature are measured simultaneously for each member of the Group. Step S806 is repeated for each member of the Group to obtain IR radiation measurements in first and second wavelength bands, as discussed above. At step S808 the normalized ratio parameter is calculated for each member of the Group from the IR radiation measurements. At step S810, steps S802, S804, S806 and S808 are repeated at various ambient temperatures and for various substance concentrations. At step S812 the body surface temperature, the ambient temperature and the normalized ratio parameter are plotted against one another and against the measured blood substance concentration for all members of the Group.

SCOPE OF THE INVENTION

The above description presents the best mode contemplated for carrying out the present system and methods for non-invasive measurement of a substance within a body and of the manner and process of practicing them, in such full, clear, concise, and exact terms as to enable any person skilled in the art to which they pertain to practice this system and these methods. This system and these methods are, however, susceptible to modifications and alternate constructions from those discussed above that are fully equivalent. Consequently, this system and these methods are not limited to the particular embodiments disclosed. On the contrary, this system and these methods cover all modifications and alternate constructions coming within the spirit and scope of the system and methods as generally expressed by the following claims, which particularly point out and distinctly claim the subject matter of the system and methods.

What is claimed is:

1. A method for measuring a concentration of a substance in a bloodstream of a body, the method comprising the steps of:

measuring a first amount of infrared (IR) radiation absorbed or emitted from the body in a first IR wavelength band in which the substance exhibits IR absorption or emission, and generating a first signal having a first radiation measurement value indicative of the first amount;

measuring a second amount of IR radiation absorbed or emitted from the body in a second IR wavelength band different from the first IR wavelength band and including wavelengths in which the substance exhibits no more than negligible IR absorption or emission, and generating a second signal having a second radiation measurement value indicative of the second amount;

measuring a temperature of a surface on the body and generating a third signal having a third value indicative of the temperature of the surface;

measuring an ambient temperature and generating a fourth signal having a fourth value indicative of the ambient temperature;

providing a memory device in which is stored an empirically-derived look-up table containing data correlating values for the concentration of the substance in the bloodstream with (a) ambient temperature values, (b) body surface temperature values, and (c) normalized radiation parameter ratio values, each of which is determined by the ratio of (1) a radiation parameter value in the first IR wavelength band normalized against a first blackbody radiation parameter value in the first IR wavelength band to (2) a radiation parameter value in the second IR wavelength band normalized against a second predetermined blackbody radiation parameter value in the second IR wavelength band;

providing a processor configured to receive the first, second, third, and fourth signals, the processor being operably associated with the memory device so as to access the lookup table therefrom; and operating the processor to (a) normalize the first radiation measurement value against the first predetermined blackbody radiation value, (b) normalize the second radiation measurement value against the second predetermined blackbody radiation value, (c) calculate a normalized radiation parameter ratio value as the ratio of the normalized first radiation measurement value to the normalized second radiation measurement value, (d) correct the normalized radiation parameter ratio value using the third and fourth values to obtain a corrected normalized radiation parameter ratio value, and (e) determine from the lookup table the concentration of the substance in the bloodstream correlated with the corrected normalized radiation parameter ratio value.

2. The method of claim 1, wherein the second IR wavelength band is the entire far IR spectrum in which the body emits and absorbs IR radiation.

3. The method of claim 1, wherein the second IR wavelength band is an IR wavelength band or bands in which the substance exhibits no more than negligible emission and absorption of IR radiation.

4. The method of claim 1, wherein the normalized ratio parameter is selected from the group consisting of at least one of the ratio of the first amount normalized against a black body to the second amount normalized against a black body, and a logarithm of the ratio of the first amount normalized against a black body to the second amount normalized against a black body.

5. The method of claim 1, wherein the substance is glucose.

6. The method of claim 1, wherein the body is a human body.

7. The method of claim 1, further comprising one of the steps of cooling the body surface to cause the substance to absorb IR, and heating the body surface to cause the substance to emit IR.

8. Apparatus for measuring a concentration of a substance in a bloodstream of a body, comprising:

an infrared (IR) radiation detection device operable to detect the IR radiation absorbed or emitted from the body, and to generate a first output signal having a first radiation measurement value indicative of a first amount of IR radiation absorbed or emitted from the body in a first IR wavelength band in which the substance exhibits IR absorption or emission, and a second output signal having a second radiation measurement value indicative of a second amount of IR radiation absorbed or emitted from the body in a second IR wavelength band different from the first IR wavelength band and including wavelengths in which the substance exhibits no more than negligible IR absorption or emission;

a first temperature sensor configured to measure a surface temperature at a surface of the body and to generate a third output signal having a third value indicative of the surface temperature;

a second temperature sensor configured to measure an ambient temperature and to generate a fourth output signal having a fourth value indicative of the ambient temperature;

a memory device in which is stored an empirically-derived look-up table containing data correlating values for the concentration of the substance in the bloodstream with (a) ambient temperature values, (b) body surface temperature values, and (c) normalized radiation parameter ratio values, each of which is determined by the ratio of (1) a radiation parameter value in the first IR wavelength band normalized against a first blackbody radiation parameter value in the first IR wavelength band to (2) a radiation parameter value in the second IR wavelength band normalized against a second predetermined blackbody radiation parameter value in the second IR wavelength band; and a processor configured to receive the first, second, third, and fourth signals, the processor being operatively associated with the memory device so as to access the lookup table therefrom;

wherein the processor is operable to (a) normalize the first radiation measurement value against the first predetermined blackbody radiation value, (b) normalize the second radiation measurement value against the second predetermined blackbody radiation value, (c) calculate a normalized radiation parameter ratio value as the ratio of the normalized first radiation measurement value to the normalized second radiation measurement value, (d) correct the normalized radiation parameter ratio value using the third and fourth values to obtain a corrected normalized radiation parameter ratio value, and (e) determine from the lookup table the concentration of the substance in the bloodstream correlated with the corrected normalized radiation parameter ratio value.

9. The apparatus of claim 8, wherein the second IR wavelength band is the entire far IR spectrum in which the body emits and absorbs IR radiation.

10. The apparatus of claim 8, wherein the second IR wavelength band is an IR wavelength band or bands in which the substance exhibits no more than negligible emission and absorption of IR radiation.

11. The apparatus of claim 8, wherein the normalized ratio parameter is selected from the group consisting of at least one of the ratio of the first amount normalized against a black body to the second amount normalized against a black body, and a logarithm of the ratio of the first amount normalized against a black body to the second amount normalized against a black body.

12. The apparatus of claim 8, wherein the substance is glucose.

13. The apparatus of claim 8, further comprising a cooling device operable to cool the body surface.

14. The apparatus of claim 8, further comprising a heating device operable to heat the body surface.

15. The apparatus of claim 8, wherein the IR radiation detection device comprises:
an IR radiation detector;
an IR filter assembly selectively operable (a) to transmit IR radiation only in the first IR wavelength band to the IR radiation detector and (b) to transmit IR radiation in the second IR wavelength band to the IR radiation detector.

16. The apparatus of claim 8, wherein the IR radiation detection device comprises:
a first IR radiation detector operable to detect IR radiation only in the first IR wavelength band; and
a second IR radiation detector operable to detect IR radiation in the second IR wavelength band.

17. The apparatus of claim 8, wherein the IR radiation detection device is operable as the first temperature sensor.

* * * * *